US005776898A

United States Patent [19]
Teicher et al.

[11] Patent Number: 5,776,898
[45] Date of Patent: Jul. 7, 1998

[54] METHOD FOR TREATING A TUMOR WITH A CHEMOTHERAPEUTIC AGENT

[75] Inventors: Beverly A. Teicher. Needham; Carl W. Rausch. Medford; Robert E. Hopkins, II. Scituate, all of Mass.

[73] Assignees: Dana-Farber Cancer Institute. Boston; Biopure Corporation. Cambridge, both of Mass.

[21] Appl. No.: 477,110

[22] Filed: Jun. 7, 1995

Related U.S. Application Data

[63] Continuation-in-part of Ser. No. 94,501, Jul. 20, 1993, which is a continuation-in-part of Ser. No. 699,769, May 14, 1991.

[51] Int. Cl.$^6$ .................... A61K 38/42; A61K 38/17; C07K 14/47; C07K 14/805
[52] U.S. Cl. .................... 514/6; 514/21; 514/908; 530/385; 530/829
[58] Field of Search .................. 574/6; 530/385, 530/829; 436/64; 514/21, 908

[56] References Cited

U.S. PATENT DOCUMENTS

| | | | |
|---|---|---|---|
| 5,084,558 | 1/1992 | Rausch et al. | 530/385 |
| 5,158,536 | 10/1992 | Sekins et al. | 604/20 |
| 5,296,465 | 3/1994 | Rausch et al. | 514/6 |
| 5,478,806 | 12/1995 | Nho | 514/6 |

FOREIGN PATENT DOCUMENTS

PCT/US87/
02967 10/1987 WIPO .

OTHER PUBLICATIONS

Yanai et al., "Antitumor Effect of Arterial Administration of a Medium-Chain Triglyceride Solution of an Angiogenesis Inhibitor". . . Pharm. Res. 12(S) 653–657 1995.

Kato et al., "Enhanced Suppresion of Tumor Growth . . . "Cancer Res. 54 5143–5147 1994.

Teicher, B. A., et al., "Perfluorochemical Emulsions Can Increase Tumor Radiosensitivity."*Science*, 223:934–936 (1984).

Chang. T.M.S., "Red Blodd Cell Substitutes: Microencpsulated Hemoglobin and Cross–Linked Hemoglobin Including Pyridoxylated Polyhemoglobin & Conjugated Hemoglobin," *Biomat., Art. Cells, Art. Org.*, 16(1–3) :11–29 (1988).

De Venuto, F., "Evaluation of Human and Bovine Modified–Hemoglobin Solution as Oxygen–Carrying Fluid for Blood Volume Replacement," *Biomat., Art. Cells, Art. Org.*, 16(1–3) :77–83 (1988).

Bucci, E., et al., "Bovine Hemoglobin as a Basis for Artificial Oxygen Carriers," *Biomat., Art. Cells, Art. Org.*, 16(1–3) :197–204 (1988).

Teicher, B.A., et al., "Effect of Various Oxgenation Conditions and Fluorosol $^R$–DA on Cancer Chemotherapeutic agents," *Biomat., Art. Cells, Art. Org.*, 16(1–3) :533–546 (1988).

Teicher, B.A., et al., "Effect of Oxygen Level on the Enhancement of Tumor Response to Radiation by Perfluorochemical Emulsions ) (PFCES) OR Hemoglobin," *Int. J. Rad. Oncol. Biol. Physic*, 19:137 (1990) (Abstract).

Teicher, B.A., et al., "Combination Treatment with a Purified Hemoglobin Preparation and Antitumor Alkylating Agents (AA) I the FSaIIC Fibrosarcoma," *Proc. Am. Assoc. Cancer Res.*, 32:387 (1991) (Abstract 2302).

Teicher, B. A., et al., "Effect of a Bovine Hemoglolin Prepartion (PBHS) on the Response of Two Murine Solid Tumors to Radiation Therapy and Chemothrapeutic Alkylating Agents," *Biomat., Art. Celss, Art. Org.*, 19(2) :491 (1991) (Abstract).

Teicher, B.A., et al., "Effect of Oxygen Level on the Enhancement of Tumor Response to Radiation by Perfluorochemical Emulsions or a Bovine Hemoglobin Preparation," *Int. J. Radiation Oncology Biol. Phys.*, 21:969–974 (1991).

Teicher, B.A., et al., "Influence of Scheduling, Dose, and Volume of Administration of a Perfluorochemical Emulsion on Tumor Response to Radiation Therapy," *Int. J. Radiat. Oncol. Biol. Phys.*, 19:945–951 (1990).

Teicher, B.A., et al., "Approaches to Defining the Mechanism of Enhancement by Fluosol–DA 20% with carbogen of Melphalan Antitumor Activity," *Cancer Research*, 47:513–518 (Jan. 15, 1987).

Teicher, B.A., et al., "Combination Treatment with a Purified Hemoglobin Preparation and Antitumor Alkylating Agents (AA) In the FSaIIC Fibrosarcoma," *Proc. Annu. Meet. Am. Assoc. Cancer Res.*, 32:A2302 (1991).

"Potentiation of Neoplasm Inhibitor Activity by Perfluorocarbon Emulsions," *Chemical Abstracts*, CA101(23): 204312S, (Jul. 27,1984).

Teicher, B.A., et al., "Increased Efficiency of Chemo–and Radio–Therapy by a Hemoglobin Solution in the 9L Gliosarcoma," in vivo, vol. 9, No. 1, 11–18 (Mar. 1995).

Holden, S.A., et al., "Increased Efficacy of Chemo–and Radio–Therapy by a Hemoglobin Solution in the 9L Gliosarcoma," from 43rd Mtg. Radiat. Res. Soc/North Amer. Hyperthermia Soc., San Jose. CA, Apr. 1995.Abstract No. P25–391, p.202.

Teicher, B.A., "Therapeutic Approaches Involving Oxygen Delivery and Antiangiogenic Agents," *Proceedings of the American Association for Cancer Research*, 35:663–664 (1994).

(List continued on next page.)

*Primary Examiner*—Nancy Degen
*Attorney, Agent, or Firm*—Hamilton, Brook, Smith & Reynolds, P.C.

[57] ABSTRACT

A method is disclosed treating a tumor in a host by administering a nonemulsified ultrapurified polymerized hemoglobin solution to the host and also administering a chemotherapeutic agent to the host. In a particularly preferred embodiment, the hemoglobin is bovine hemoglobin.

14 Claims, 2 Drawing Sheets

OTHER PUBLICATIONS

Teicher, B.A., "Increase in Tumor Oxygenation by Antiangiogenesis and Oxygen Delivery Agents as Determined by Electrode Measurements," from 43rd Mtg. Radiat. Res. Soc/North Amer. Hyperthermia Soc., San Jose, CA, Apr. 1995, Abstract No. S31–2, p. 103.

Teicher, B.A., et al., "Potentiation of Cytotoxic Cancer Therapies by TNP–470 Alone and with Other Anti–Angiogenic Agents," *Int. J. Cancer,* 57:920–925 (1994).

Teicher, B.A., et al., "Minocycline as a Modulator of Chemotherapy and Hyperthermia in Vitro and in Vivo," *Cancer Lettters,* 82:17–25 (1994).

Teicher, B.A., et al., "Response of FSaII Fibrosarcoma to Antiangiogenic Modulators plus Cytoxic Agents," *Anticancer Research,* 13:2101–2106 (1993).

Teicher, B.A., et al., "β–Cyclodextrin Tetradecasulfate/Tetrahydrocortisol ± Minocycline as Modulators of Cancer Therapies in Vitro and in Vivo Against Primary and Metastatic Lewis Lung Carcinoma," *Cancer Chemother. Pharmaol.,* 33:229–238 (1993).

Teicher, B.A., et al., "Effect of a Bovine Hemoglobin Preparation on the Response of the FSaIIC Fibrosarcoma to Chemotherapeutic Alkylating Agents," *J. Cancer Res. Clin. Oncol.,* 118:123–128 (1992).

Teicher, B.A., et al., "Fluosol–DA/Carbogen with Lonidamine or Pentoxifylline as Modulators of Alkylating Agents in the FSaIIC Fibrosarcoma," *Cancer Chemother. Pharmacol.,* 28:45–50. (1991).

Teicher, B.A., et al., "Classification of Antineoplastic Treatments by Their Differential Toxicity Toward Putative Oxygenated and Hypoxic Tumor Subpopulations in Vivo in the FSaIIC Murine Fibrosrcoma," *Cancer Research,* 50:3339–3344 (1990).

Gruber, M. et al., "Phase I/II Study of Fluosol®/$O_2$ in Combination with BCNU in Malignant Glioma". From *Proceedings of the American Association for Cancer Research,* 31:190 (1990) , Abstract No. 1129.

Meyers, F., et al. "Phase I/II Study of Fluosol®/Oxygen in Combination With Weekly 5–Fluorouracil (5FU) in Metastatic Colorectal Carcinoma". From *Proceedings of the American Association for Cancer Research,* 30:256 (1989), Abstract No. 1020.

Garewal, H., "Fluosol®/Oxygen in Combination with Cyclophosphamide in Advanced Non–Small Cell Lung Carcinoma (NSCLC) : Phase I Results." From *Proceedings of the American Association for Cancer Research,* 30:371 (1989) , Abstract No. 1078.

Martin, D.F. et al., "Potentiation of Rat Brain Tumor Therapy by Fluosol and Carbogen," NCI Monographs, *NCI Monographs,* 6:119–122 (1988).

Teicher, B.A., "Efficacy of Bleomycin with Hyperbaric Oxygen or Extended Carbogen Breathing in the Presence and Absence of Fluosol–DA." From *Proceedings of AACR,* 29:483 (1988) , Abstract No. 1919.

Teicher, B.A., et al., "Effect of Fluosol–DA/Carbogen on Etoposide/Alkylating Agent Antitumor Activity," *Cancer Chemother. Pharmacol.,* 21:281–285 (1988).

Teicher, B.A., et al., "Effects of Fluosol–DA and Oxygen Breathing on Adriamycin Antitumor Activity and Cardiac Toxicity in Mice," *Cancer,* 61(11) : 2196–2201 (1988).

Teicher, B.A., et al., "The Effect of Fluoson–DA and Oxygentaion Status on the Activity of Cyclophosohamide in Vivo," *Cancer Chemother. Pharmacol.,* 21:286–291 (1988).

Teicher, B.A., et al., "Effect of Fluosol–DA® on the Response of Intracranial 9L Tumors to X Rays and BCNU," *Int. J. Radiation Oncology Biol. Phys.,* 15:1187–1192 (1988).

Teicher, B.A., et al., "Effects of Various Oxygenation Conditions on the Enhancement by Fluosol–DA of Melphalan Antitumor Activity," *Cancer Research,* 47:5036–5041 (1987).

Teicher, B.A., and Holden, S.A., "Survey of the Effect of Adding Fluosol–DA 20%/$O_2$ to Treatment With Various Chemotherapeutic Agents," *Cancer Treatment Reports,* 71(2) :173–177 (1987).

Teicher, B.A., "Use of Fluosol–DA®on Cancer Therapy," *Int. Med. Specialist,* 8:190–199 (1987).

Teicher, B.A., et al., "Effect of Fluosol–DA/$O_2$ on Tumor–Call and Bone–Marrow Cytoxicity of Nitrosoureas in Mice Bearing FSA–11 Fibrosarcoma," *Int. J. Cancer,* 38:285–288 (1986).

Teicher, B.A., et al., "Effect of Fluosol–DA/$O_2$ on the Antitumor Activity and Pulmonary Toxicity of Bleomycin," *Cancer Chemother. Pharmacol.,* 18:213–218 (1986).

Teciher, B.A., et al., "Differential Enhancement of Melphalan Cytotoxicity in Tumor and Normal Tissue by Fluosol–DA® and Oxygen Breathing," *Int. J. Cancer:* 36:585–589 (1985).

Teicher, B.A., et al., "Effect of Oxygen on the Cytoxicity and Antitumor Activity of Eptoposide," *JNCI,* 75(6) :1129–1133 (1985).

Teicher, B.A., "Effect of the Addition of Fluosol–DA/$O_2$ on Tumor Growth Delay and Tumor Cell and Bone Marrow Killing Caused by Various Nitrosoureas in Mice Bearing FSaII Fibrosarcoma," Presented at the meeting of the Chemical Modifiers of Cancer treatment Conference; Clearwater FL (1985, Oct.) 4–13.

Teicher, B.A. and Rose, C.M., "Oxygen–Carrying Perfluorochemical Emulsion as an Adjuvant to Radiation Therapy in Mice," *Cancer Research* 44:4285–4288 (1984).

Teicher, B.A, and Rose, C.M., "Enhancement of Anticancer Drug Efficacy by a Perfluorocarbon Emulsion (PFC) ."From *ACR Proceedings,* 25:316 (1984) , Abstract No. 1251.

Alvarez Sotomayor, E., et al., "Minocycline in Combination with Chemotherapy or Radiation Therapy in Vitro and in Vivo," *Cancer Chemother. Pharmacol.* 30:377–384 (1992).

Teicher, B.A. et al., "Antiangiogenic Agents Potentiate Cytoxic Cancer Therapies Against Primary and Metastatic Disease," *Cancer Research* 52:6702–6704 (1992).

Alvarez Sotomayor, E., et al., "14–$SO_4$ –β–Cyclodextrin (SCD)/ Tetrahydrocortisol (THC) and/or minocycline (MINO) as Modulators of Antitumor Agents." From *Proceedings of the American Association for Cancer Research,* 33:420 (1992) , Abstract No. 2506.

Teicher, B.A., et al., "Increased Tumor Oxygenation and Radiation Sensitivity in the Lewis Lung Carcinoma After a Perflubron Emulsion/Carbogen and Antiangiogenic Agents." From *Artif. Cells Blood Substitutes Immobulization Biothechnol.* 22(5) : (1994) , Abstract No. A169.

Teicher, B.A., et al., "Definition and Manipulation of Tumor Oxgenation," *Radiation Oncology Investigation,* 2:66–76 (1994).

Teicher, B.A. et al., "Oxygenation of Tumors bya Hemoglobin Solution," *J. Cancer Res. Clin. Oncol,* 120:85–90 (1993).

Kennedy, K.A., et al., "the Hypoxic Tumor Cell: A Target For Selective Cancer Chemotherapy," *Biochemical Pharmacology,* 29:1–8 (1980).

Adams, G.E., "The Clinical Relevance of Tumor Hypoxia," *Eur. J. cancer,* 26(4) :420–421 (1990).

Teicher, B.A., "Hypoxia and Drug Resistance," *Cancer and Metastasis Reviews,* 13:139–168 (1994).

METHOD FOR TREATING A TUMOR WITH A CHEMOTHERAPEUTIC AGENT

Related Applications

This is a Continuation-In-Part of U.S. Ser. No. 08/094,501, filed Jul. 20, 1993, which is a Continuation-In-Part of U.S. Ser. No. 07/699,769, filed May 14, 1991, now abandoned, which are hereby incorporated in their entirety by reference.

GOVERNMENT SUPPORT

Work relating to the invention described and claimed herein was partially supported by Grant No. P01-19589 from the National Institutes of Health and by Grant No. P01-CA38493 from the National Cancer Institute.

BACKGROUND OF THE INVENTION

Solid tumor masses in cancer patients have been found to be heterogeneous in oxygenation and to contain regions of hypoxia. See Vaupel, P., "Oxygenation of Human Tumors", Strahlenther. Onkol. 166:377–386 (1990); and Adams, G. E., The Clinical Relevance of Tumour Hypoxia, 26(4):420–421 (1990). Recent studies in human tumors with oxygen electrodes have reaffirmed the occurrence of significant hypoxic areas within human tumors. Vaupel, P. ibid; Kallinowski, F. et al., "Tumor Tissue Oxygenation as Evaluated by Computerized-pO$_2$-Histography", Int. J. Radiat. Oncol. Biol. Phys. 19:953–961 (1990); and Gatenby, R. A. et al., "Oxygen Distribution in Squamous Cell Carcinoma Metastases and Its Relationship to Outcome of Radiation Therapy", Int. J. Radiat. Oncol. Biol. Phys. 14:831–838 (1988). Preclinical studies, both in vitro and in vivo, have established that hypoxia protects tumor cells from the cytotoxic actions of radiation and chemotherapeutic agents and thereby may be a significant factor in therapeutic resistance. Adams, G. E. ibid; Sartorelli, A. C., "Therapeutic Attack of Hypoxic Cells of Solid Tumors: Presidential Address", Cancer Res. 48:775–778 (1988); Teicher, B. A. et al., "Classification of Antineoplastic Agents by Their Selective Toxicities Toward Oxygenated and Hypoxic Tumor Cells", Cancer Res. 41:73–81 (1981); and Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", Cancer Res. 50:3339–3344 (1990).

Increased delivery of oxygen from the lungs can be a useful way of improving the oxygenation of solid tumor masses by altering the gradient of oxygen as it is absorbed from the vasculature and distributed into the tissue. Because of this, one strategy which has been attempted to overcome the problem of hypoxia in treating tumors involves the use of perfluorocarbon emulsions with oxygen or carbogen (95% oxygen/5% carbon dioxide) breathing. Holden, S. A. et al., "Addition of a Hypoxic Cell Selective Cytotoxic Agent (mitomycin C or porfiromycin) to Treatment with Fluosol®-DA/Carbogen/Radiation", Radiother. Oncol. 18:59–70 (1990); Teicher, B. A. et al., "The Effect of Fluosol-DA and Oxygenation Status on the Activity of Cyclophosphamide In Vivo" Cancer Chemother. Pharmacol. 21:286–291 (1988); Martin, D. F. et al., "Enhancement of Tumor Radiation Response by the Combination of a Perfluorochemical Emulsion and Hyperbaric Oxygen", Int. J. Radiat. Oncol. Biol. Phys. 13:747–751 (1987); Teicher, B. A. and C. M. Rose, "Perfluorochemical Emulsion Can Increase Tumor Radiosensitivity" Science 223:934–936 (1984); and Teicher, B. A. et al., "Optimization of Perfluorochemical Levels with Radiation Therapy" Cancer Res. 49:2693–2697 (1989). In preclinical solid tumor models, the use of perfluorocarbon emulsions with carbogen or oxygen breathing in conjunction with radiation therapy has produced positive results. Teicher, B. A. and C. M. Rose, ibid, Teicher, B. A. et al., ibid; Teicher, B. A. and C. M. Rose, "Oxygen-Carrying Perfluorochemical Emulsion as an Adjuvant to Radiation Therapy in Mice", Cancer Res. 44:4285–4288 (1984); Teicher, B. A. and C. M. Rose, "Effect of Dose and Scheduling on Growth Delay of the Lewis Lung Carcinoma Produced by the Perfluorochemical Emulsion, Fluosol-DA", Int. J. Radiat. Oncol. Biol. Phys. 12:1311–1313 (1986); Teicher, B. A. et al., "Influence of Scheduling Dose and Volume of Administration of the Perfluorochemical Emulsion Therox® on Tumor Response to Radiation Therapy", Int. J. Radiat. Oncol. Biol. Phys., in press (1991); Teicher, B. A. et al., "Effect of Fluosol®-DA on the Response of Intracranial 9L Tumors to X-rays and BCNU", Int. J. Radiat. Oncol. Biol. Phys. 15:1187–1192 (1988); Lee, I. et al., "Effects of Fluosol-DA and Carbogen on the Radioresponse of SCK Tumors and Skin of A/J Mice", Radiat. Res. 112:173–182 (1987); Martin, D. F. et al., "Effect of a Perfluorochemical Emulsion on the Radiation Response of BA 1112 Rhabdomysarcomas", Radiat. Res. 112:45–53 (1987); Moulder, J. E. et al., "Applicability of Animal Tumor Data to Cancer Therapy in Humans", Int. J. Radiat. Oncol. Biol. Phys. 14:913–927 (1988); Moulder, J. E. and B. L. Fish, "Tumor Sensitization by the Intermittent use of Perfluorochemical Emulsions and Carbogen Breathing in Fractionated Radiotherapy", In: E. M. Fielden, J. F. Fowler, J. H. Hendry and D. Scott (eds.), Proceedings of the 8th International Congress of Radiation Research, Vol. 1, p. 299, London: Taylor and Francis, Inc. (1987); Rockwell, S. et al., "Reactions of Tumors and Normal Tissues in Mice to Irradiation in the Presence and Absence of a Perfluorochemical Emulsion" Int. Radiat. Oncol. Biol. Phys. 112:1315–1318 (1986); Song, C. W. et al., "Increase in pO$_2$ and Radiosensitivity of Tumors by Fluosol®-DA (20%) and Carbogen", Cancer Res. 47:442–446 (1987); and Zhang, W. L. et al., "Enhancement of Tumor Response to Radiation by Fluosol-DA", Int. J. Radiat. Oncol. Biol. Phys. 10:172–175 (1984).

Further, some initial clinical trials of the perfluorochemical emulsion, Fluosol®-DA, and oxygen breathing with radiation therapy have been carried out and some are still underway. Rose, C. M. et al., "A Clinical Trial of Fluosol®-DA 20% in Advanced Squamous Cell Carcinoma of the Head and Neck", Int. J. Radiat. Oncol. Biol. Phys. 12:1325–1327 (1986); Lustig, R. et al., "Phase I–II Study of Fluosol-DA and 100% Oxygen Breathing as an Adjuvant to Radiation in the Treatment of Advanced Squamous Cell Tumors of the Head and Neck", Int. J. Radiat. Oncol. Biol. Phys. 16:1587–1594 (1989); Lustig, R. et al., "Phase I/II Study of Fluosol and 100% Oxygen Breathing as an Adjuvant to Radiation in the Treatment of Unrespectable Non Small Cell Carcinoma of the Lung", Int. J. Radiat. Oncol. Biol. Phys., 17s1:202 (1989); and Evans, R. G. et al., "A Phase I–II Study of the Use of Fluosol®-DA 20% as an Adjuvant of Radiation Therapy in the Treatment of Primary High-Grade Brain Tumors", Int. J. Radiat. Oncol. Biol. Phys., 1721:175 (1989).

The effect of perfluorocarbon emulsions in carbogen or oxygen breathing with certain chemotherapeutic agents has also been studied in preclinical solid tumor models. Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", *Cancer Res.* 50:3339–3344 (1990); Holden, S. A. et al., "Addition of a Hypoxic Cell Selective Cytotoxic Agent (Mitomycin C or Porfiromycin) to Treatment with Fluosol-DA®/Carbogen/Radiation", *Radiother. Oncol.* 18:59–70 (1990); Teicher, B. A. et al., "The Effect of Fluosol-DA and Oxygenation Status on the Activity of Cyclophosphamide in vivo" *Cancer Chemother. Pharmacol.* 21:286–291 (1988); Teicher, B. A. et al., "Approaches to Defining the Mechanism of Fluosol-DA 20%/Carbogen Enhancement of Melphalan Antitumor Activity", *Cancer Res.* 47:513–518 (1987); Teicher, B. A. et al., "Differential Enhancement of Melphalan Cytotoxicity in Tumor and Normal t+Tissue by Fluosol-DA and Oxygen Breathing", *Int. J. Cancer* 36:585–589 (1985); Teicher, B. A. et al., "Effects of Various Oxygenation Conditions on the Enhancement by Fluosol-DA of Melphalan Antitumor Activity", *Cancer Res.* 47:5036–5041 (1987); Teicher, B. A. and S. A. Holden, "A Survey of the Effect of Adding Fluosol-DA 20%/ $O_2$ to Treatment with Various Chemotherapeutic Agents", *Cancer Treat. Rep.* 71:173–177 (1987); Teicher, B. A. et al., "Effect of Various Oxygenation Conditions and Fluosol-DA on Cancer Chemotherapeutic Agents", *Biomat., Art. Cells and Art. Organs* 16:533–546 (1988); Teicher, B. A. et al., "Effect of Oxygen on the Cytotoxicity of Antitumor Activity of Etoposide", *J. Natl. Cancer Inst.* 75:1129–1133 (1985); Teicher, B. A. et al., "Effect of Fluosol-DA/$O_2$ on Tumor Cell and Bone Marrow Cytotoxicity of Nitrosoureas in Mice Bearing FSaII Fibrosarcoma", *Int. J. Cancer* 38:285–288 (1986); Teicher, B. A. et al., "Effect of Fluosol-DA/$O_2$ on the Antitumor Activity and Pulmonary Toxicity of Bleomycin", *Cancer Chemother. Pharmacol.* 18:213–218 (1986); Teicher, B. A. et al., "Effects of Fluosol®-DA and Oxygen Breathing on Adriamycin Antitumor Activity and Cardiac Toxicity in Mice", *Cancer* 61:2196–2201 (1988); Teicher, B. A. et al., "Effect of Carious Oxygenation Conditions and Fluosol®-DA on the Cytotoxicity and Antitumor Activity of Bleomycin", *J. Natl. Cancer Inst.* 80:599–603 (1988); Teicher, B. A. et al., "Effect of Fluosol-DA/Carbogen on Etoposide/Alkylating Agent Antitumor Activity", *Cancer Chemother. Pharmacol.* 21:281–285 (1988); Martin, D. F. et al., "Potentiation of Rat Brain Tumor Therapy by Fluosol and Carbogen", *NCI Monogr.* 6:119–122 (1988); and Kim, G. E. and C. W. Song, "The Influence of Fluosol-DA and Carbogen Breathing on the Antitumor Effects of Cyclophosphamide In Vivo", *Cancer Chemother. Pharmacol.* 25:99–102 (1989). With many chemotherapeutic agents, very positive therapeutic results have been obtained and several initial clinical trials have been carried out with Fluosol®-DA and oxygen breathing with single anticancer drugs. See Gruber, M. et al., "Phase I/II Study of Fluosol®/$O_2$ in Combination with BCNU in Malignant Glioma", *Proc. Amer. Assoc. Cancer Res.* 31:190 (March 1990); Carewal, H. et al., "Fluosol®/Oxygen in Combination with Cyclophosphamide in Advanced Non-Small Cell Lung Carcinoma (NSCLC): Phase I Results", *Proc. Amer. Assoc. Cancer Res.* 30:271 (March 1989); and Meyers, F. et al., "Phase I/II Study of Fluosol®/Oxygen in Combination with Weekly 5-Fluorouracil (5FU) in Metastatic Colorectal Carcinoma", *Proc. Amer. Assoc. Cancer Res.* 30:256 (March 1989).

Despite the initial success with the use of perfluorocarbon emulsions, combined with carbogen or oxygen breathing in conjunction with chemotherapeutic agents, these techniques have not proven entirely satisfactory. For example, perfluorocarbons have very limited oxygen-transport capability at ambient oxygen pressures. Blood delivers approximately 6% (v/v) oxygen to tissues at ambient pressures, whereas, at these same pressures, perfluorocarbon emulsions can only deliver about 2% (v/v). Furthermore, generally perfluorocarbons only enhance the anti-tumor effects of the chemotherapeutic agents while retained in the body and only while breathing an enriched supply of oxygen, such as pure oxygen or carbogen. When not breathing enriched oxygen, perfluorocarbons typically do not enhance the effect of chemotherapeutic agents. In addition, the retention time of most perfluorocarbons in the body is unacceptably low.

Thus, the need exists for a method of enhancing the effects of antitumor chemotherapeutic agents for longer periods of time while breathing air or oxygen-enriched atmospheres.

SUMMARY OF THE INVENTION

This invention relates to a method for treating a tumor in a host, including a human being, with a chemotherapeutic agent. In this method, a nonemulsified ultrapurified polymerized hemoglobin solution is administered to the host in an amount which significantly increases the antitumor effect of the chemotherapeutic agent. An effective amount of the chemotherapeutic agent is also administered to the host. In a particularly preferred embodiment, the hemoglobin is bovine hemoglobin.

The advantages of administering a nonemulsified ultrapurified polymerized hemoglobin solution with a chemotherapeutic agent include a significant improvement in tumor oxygenation and an increase in the antitumor effect of the chemotherapeutic agent even without carbogen or pure oxygen breathing therapy. This enhanced effect can occur while just breathing air. Thus, while sufficient amounts of the chemotherapeutic agent and of the polymerized hemoglobin solution are in the body, the antitumor effect will be enhanced. In addition, as hemoglobin is able to chelate and deliver oxygen under air-breathing conditions, oxygen toxemia, which can occur with the use of perfluorocarbon emulsions, is eliminated by the use of the hemoglobin solution. Further, polymerized hemoglobins typically have a longer circulating half-life than many of the perfluorocarbon emulsions and, therefore, have a longer functional period post-administration. The acidic environments in tumors increases the off-loading of oxygen and, therefore, the oxygen delivery from hemoglobin, as should temperature elevation (i.e., clinical hyperthermia). Hemoglobin solutions also have less retention in normal tissues, which is a concern with many perfluorocarbon preparations.

DETAILED DESCRIPTION OF THE INVENTION

This invention relates to a method for treating a tumor in a host. The host can be any species which develops solid tumors or masses of tumor cells containing oxygen heterogeneity. Examples of hosts include but are not limited to, reptiles, amphibians, avians and mammals, including human beings, as well as domestic animals such as dogs, cats, cows and horses.

Tumors treatable by this method include those in which oxygen heterogeneity, including regions of hypoxia, protect tumor cells against the cytotoxic action of chemotherapeutic agents. These are usually solid tumors, such as sarcomas, carcinomas, lymphomas, etc. However, in certain cases of dispersed tumor cells, such as advanced leukemia, masses of tumor cells form which can produce regions of oxygen heterogeneity, as well.

As used herein, the term "chemotherapeutic agent" is employed to include chemical and biological agents, including small molecules and larger molecules, such as peptides, proteins, lymphokines, antibodies, tumor necrosis factor, conjugates of antibodies with toxins, and other chemical or biological molecules which have an antitumor effect which is oxygen dependent.

There are a variety of known classes of small molecule antitumor chemotherapeutic agents. These include alkylating agents, such as Melphalan (PAM), Cyclophosphamide (CTX), cis-Diammminedichloroplatinum (II) (CDDP) and N,N'-bis(II-chloroethyl)-N-nitrosourea (BCNU). Another general class of antitumor chemotherapeutic agents are the antimetabolites, such as 6-Mercaptopurine, 5-fluorouracil (5-FU), fluorodeoxyuridine, cytosine arabinoside, methotrexate and thioquinone. Antibiotics are another general class of antitumor chemotherapeutic agents including drugs such as actinomycin, daunorubicin, adriamycin and bleomycin. Still yet another class is the vinca alkaloids, including etoposide, vincristine and vinblastine.

Mixtures of more than one antitumor chemotherapeutic agent can, of course, be administered. Indeed, it is often preferred to use mixtures or sequential administration of different antitumor agents to treat tumors, especially agents from the different classes of agents. For example, mixtures of methotrexate and a cis-platinum compound are often used to treat various tumors.

The chemotherapeutic agent can be administered to the host parenterally, for example, by subcutaneous, intravenous or intramuscular injection or by absorption through a bodily tissue, such as the digestive tract, the respiratory system or the skin. The form in which the antitumor agent is administered (e.g., capsule, tablet, solution, emulsion) will depend, at least in part, on the route by which it is administered.

The chemotherapeutic agent is administered in a therapeutically effective amount. This amount will be determined on an individual basis and will be based, at least in part, on consideration of the host's size, the specific tumor to be treated, the severity of the symptoms to be treated, the results sought, and other such considerations. An effective amount can be determined by one of ordinary skill in the art employing such factors and using no more than routine experimentation.

In one embodiment, in order to increase oxygen transport to the site of a tumor, a nonemulsified ultrapurified polymerized hemoglobin solution (UPHS) is administered to the host. Although not essential, it is preferred to administer the UPHS prior to administration of the antitumor agent. Also, the hemoglobin solution is preferably administered intravenously so that it is taken up into the bloodstream of the host immediately.

The amount of time between the administration of the hemoglobin solution and chemotherapeutic agent will depend upon factors such as the amount of time it takes the hemoglobin solution to be fully incorporated into the circulatory system of the host and the retention time of the hemoglobin solution in the host's body. Since UPHS has been found to remain in the host's blood stream for up to at least 48 hours, a variety of times during this period are sufficient.

Hemoglobin sufficient for UPHS can be derived from a wide variety of sources. These sources include human blood, such as outdated blood bank supplies. Additionally, hemoglobin can be derived from a variety of mammalian sources such as horses, pigs, cows, sheep, etc.

In a preferred embodiment, the hemoglobin will be derived from a species in which the hemoglobin is chloride ion-dependent for oxygen transport rather than dependent upon 2,3-diphosphoglycerate (2,3-DPG) or other phosphate molecules. This is because 2,3-DPG, present in human red blood cells, is not available freely in the circulatory system of the host to effect oxygen uptake and release for hemoglobin solutions administered according to this invention. Thus, it is preferred to employ a hemoglobin which is chloride ion-dependent for oxygen transport, such as those hemoglobins derived from sheep, goats, cows and cats. See Bunn, H. F., "Differences in the Interaction of 2,3-Diphosphoglycerate with Certain Mammalian Hemoglobins", *Science* 172:1049–50 (1971); Breepoel, P. M. et al., "Interaction of Organic Phosphates with Bovine Hemoglobin—I Oxylabile and Phosphate Labile Proton Binding", *Pflugers Arch.* 389:219–25 (1981); and Fronticelli, C. et al., "Solvent Regulation of Oxygen Affinity and Hemoglobin—Sensitivity of Bovine HemoGlobin to Chloride Ions", *J. Biol. Chem.* 259:10841–4 (1984). Bovine hemoglobin is particularly preferred because of its proven ability to transport oxygen in human beings and other mammals, in a chloride-ion dependent way, and because of its low antigenicity in human beings when it has been ultrapurified.

In order to increase the useful life of hemoglobin in the circulation, it is polymerized or cross-linked by a variety of techniques. Cross-linking agents include dialdehydes, such as glyoxal, malonic dialdehyde, succinic dialdehyde, glutaraldehyde, adipaldehyde, 3-methyl-glutaraldehyde, propyladipaldehyde, phthalic dialdehyde, terephthaldehyde and malonic dialdehyde have been employed. See, in this regard, Bonsen et al., U.S. Pat. Nos. 4,001,200; 4,001,401; and 4,053,590; Bonhard et al., U.S. Pat. Nos. 4,136,093 and 4,336,248; the teachings of each of which are incorporated herein by reference.

The polymerized hemoglobin solution is ultrapurified by various filtration and chromatographic procedures which have been described heretofore in the art. An ultrapure hemoglobin solution, according to this invention, is a hemoglobin solution which is substantially free of stroma, endotoxin, other pyrogenic substances, phospholipids, immunoglobulins and cellular-contained enzymes.

A particularly preferred nonemulsified ultrapure polymerized hemoglobin solution is based upon bovine hemoglobin. Such a bovine blood substitute has an endotoxin concentration of less than 0.5 endotoxin units/ml as measured by the LAL test; a phospholipid concentration of less than about 1 nanogram/milliliter and has a molecular weight distribution greater than 90% in the range of 65,000–1,000,000 daltons. This bovine hemoglobin solution also has an osmolarity measured by freezing point depression in the range of 180–320 milliosmols per liter; a hemoglobin content of 5–25 grams per deciliter; a met hemoglobin content of less than 20%; a $p_{50}$ in the range of 18–37 mmHg; an intravascular half life of at least two days; a cross-linking profile on gel permeation chromatography of greater than 70% cross-linked.

Such nonemulsified ultrapurified polymerized bovine hemoglobin solution is made and sold by Biopure Corporation, Boston, Mass. under the trademark Hemopure. This and other ultrapurified hemoglobin solutions are described in U.S. Pat. No. 5,084,558 issued to Rauscha et al., the teachings of which are hereby incorporated by reference.

Appropriate dosages of UPHS can be determined by those skilled in the art using routine experimentation. The dose employed in the murine studies in the Examples herein was 8–12 ml/kg, which is 9%–15% of the estimated circulatory volume. This dose corresponds to 500–750 ml as the comparative human dose or 11%–19% of estimated circulatory volume. Multiple doses of UPHS, for example one before each chemotherapy treatment, are, of course, useful with this invention and can be preferred in many cases.

In another embodiment UPHS is administered contemporaneously with treatment with an enzyme cyclo oxygenase inhibitor. Examples of said inhibitors include non-steroidal anti-inflammatory drugs (NSAID), such as minocycline hydrochloride (Mino), Diflunisal (Diflun) or Sulindac (Sulin). The addition of an enzyme cyclo oxygenase inhibitor to the treatment enhances the anti-tumor affects of the chemotherapeutic agent by blocking the metabolism of arachidonic acid to inhibit cell regulation processes.

Appropriate dosages of NSAIDS can be determined by those skilled in the art using routine experimentation. The dose employed in the murine studies in the Examples herein was a 10 mg/kg dose given daily.

The techniques for treating tumors described herein can be employed at normal body temperatures or at elevated body temperatures (hyperthermia).

Although not required, it is sometimes preferred to have the host breathe oxygen-enriched gas prior to and/or post administration of the anti-tumor therapeutic agent. This can be done by having the host breath oxygen-enriched air, 100% oxygen or carbogen (95% oxygen/5% CO2), or in certain cases exposing the host to hyperbaric oxygen conditions.

In a further embodiment, antiangiogenic agents, such as TNP-470 and minocycline, alone or in combination with hemoglobin/carbogen, are administered with a cytotoxic agent, resulting in increased efficacy of chemotherapy and radiotherapy. As described in Example VIII, tissue oxygen tensions were measured in the rat 9L gliosarcoma under conditions of normal air breathing or carbogen breathing and after intravenous administration of a hemoglobin solution with air breathing or carbogen breathing. Administration of the hemoglobin decreased the level of hypoxia in the tumors. Treatment of the animals with the antiangiogenic combination of TNP-470 and minocycline also increased tumor oxygenation compared with untreated controls. Treatment with the antiangiogenic agents along with administration of the hemoglobin solution/carbogen breathing decreased the hypoxic fraction (% $pO_2$ readings $\leq 5$ mmHg) from 71% to 30%. Treatment of the tumor-bearing animals with BCNU or adriamycin modestly reduced hypoxia in the tumors, while treatment with fractionated radiation markedly increased hypoxia in the tumors. Tumor growth delay was used to assess the response of the subcutaneous tumor to the various treatment combinations. There was a strong correlation between increased therapeutic response and decreased tumor hypoxia. Tumor growth delay from BCNU increased from 5.3 days to 16.4 days with TNP-470/ -minocycline/ hemoglobin solution/carbogen. Similarly, the tumor growth delay from adriamycin increased from 3.9 days to 17.0 days with TNP-470/minocycline/hemoglobin solution/carbogen. Finally, the tumor growth delay from fractionated radiation increased from 4.8 days to 13.3 days with TNP-470/ minocycline/hemoglobin solution/carbogen. When etanidazole was added to the complete radiation regimen, the tumor growth delay increased further to 20.5 days. These data show that the addition of non-toxic agents that increase tumor oxygenation to cytotoxic therapies can markedly increase therapeutic response.

This invention will now be further and more specifically described by the following examples.

Example I

FSaII Fibrosarcoma Growth

The FsaII fibrosarcoma (FSaIIC), adapted for growth in culture, was employed. See Rice, L. et al., "The Radiosensitivity of a Murine Fibrosarcoma as Measured by Three Cell Survival Assays", Br. J. Cancer 41:240–245 (1980). $2 \times 10^6$ FSaIIC cells, prepared from a brei of several stock tumors, were implanted intramuscularly into the legs of 8- to 10-week old male C3H/FeJ mice (The Jackson Laboratory, Bar Harbor, Me.). When the tumors were approximately 100mm$^3$ in volume, 0.3 ml (12 ml/kg; 1.32 gm protein/kg) of UPHS was injected via the tail vein. -The UPHS solution was obtained from Biopure Corporation, Boston, Mass. and was a polymerized form of a highly purified bovine hemoglobin solution. It contained 11±2 gm/deciliter of bovine hemoglobin. Measurements of $p_{50}$ for the UPHS in three assay systems and under conditions designed for testing human hemoglobin gave values of 17 mmHg to 23 mmHg. The hemoglobin content had a molecular weight of range from 68,000 to 1,000,000 (w/v). It contained sodium (145 mM/L), chloride (140 mM/L) and potassium (4.0 mM/L) in a buffer solution (pH 7.8±0.4). The circulating half life of this UPHS was about 2.5 days. DeVenuto, F., "Evaluation of Human and Bovine Modified-Hemoglobin Solution as Oxygen-Carrying Fluid for Blood Volume Replacement", Biomat. Art. Cells. Art. Org. 16:77–82 (1988); and Winslow, R. M., "Optimal Hematologic Variables for Oxygen Transport Including $p_{50}$, Hemoglobin Cooperativity, Hematocrit, Acid-Base Atatus, and Cardiac Function", Biomat., Art. Cells and Art. Organs 16:149–172 (1988).

Immediately after the administration of UPHS, 10 mg/kg Melphalan (PAM), 150 mg/kg Cyclophosphamide (CTX), 10 mg/kg cis-diaminodichloroplatinum(II) (CDDP) or 15 mg/kg N,N-bis(2-chloroethyl)-N-nitrosourea (BCNU) was administered by intraperitoneal injection of 0.2 ml of phosphate buffered normal saline containing the drug. CTX and PAM were purchased as pure powders from Sigma Chemical Company, St. Louis, Mo. CDDP was obtained as a gift from Bristol Meyers-Squibb Company, Wallingford, Conn. BCNU (Carmustine) was purchased from the Dana-Farber Cancer Institute Pharmacy.

The mice were allowed to breath air or were placed in a circulating atmosphere of 95% $O_2$/5% $CO_2$ (carbogen) for six hours and then removed to air. The progress of each tumor was measured three times weekly until it reached a volume of 500 mm$^3$. Tumor growth delay was calculated as the days taken by each individual tumor to reach 500 mm$^3$ compared to the untreated controls. Each treatment group had seven animals and the experiment was repeated three times. Days of tumor growth delay are the mean ± SE for the treatment group compared to the control.

Data on the delay of tumor growth were analyzed with a BASIC program for the Apple II minicomputer. The program derives the best fit curve for each set of data, then calculated the median, mean and standard error of the mean for individual tumor volumes and the day on which each tumor reached 500 mm$^3$. Statistical comparisons were made with Dunn Multiple Comparisons Test.

The results of these tumor growth delay experiments are presented below in Table I.

TABLE I

TUMOR GROWTH DELAYS (DAYS)

| Treatment Group | Alkylating Agent (alone) | UPHS/Air | Carbogen | UPHS/Carbogen |
|---|---|---|---|---|
| PAM(10 mg/kg) | 3.1 ± 0.5 | 6.9 ± 1.0 | 4.0 ± 0.6 | 11.1 ± 1.3 |
| CTX(150 mg/kg) | 3.6 ± 0.4 | 7.4 ± 0.7 | 5.0 ± 0.5 | 16.5 ± 1.8 |
| CDDP(10 mg/kg) | 7.4 ± 0.8 | 9.6 ± 1.1 | 7.6 ± 0.3 | 14.1 ± 1.6 |
| BCNU(15 mg/kg) | 2.5 ± 0.3 | 3.8 ± 0.5 | 3.3 ± 0.3 | 5.7 ± 0.9 |

Neither UPHS/Air nor UPHS/carbogen, without a cytotoxic agent, had any effect on the growth of the FSaIIC fibrosarcoma. The addition of UPHS to treatment with PAM resulted in a 2.2-fold increase in the tumor growth delay produced by PAM from about 3 days to about 7 days. Although carbogen breathing (6 hours) resulted in a small increase in tumor growth delay compared with PAM and air breathing, the combination of UPHS and carbogen produced a 3.6-fold increase in the tumor growth delay compared with PAM alone. The addition of UPHS to treatment with a single dose of CTX resulted in a 2.1-fold increase in the tumor growth delay produced by CTX alone. Breathing a carbogen atmosphere for 6 hours post drug administration resulted in a small increase in the tumor growth delay produced by CTX; however, the combination of UPHS and carbogen breathing was much more effective resulting in a 4.6-fold increase in tumor growth delay to about 16.5 days from 3.6 days for the drug alone.

The tumor growth delay produced by CDDP was less affected by the addition of UPHS to treatment with the drug than was either PAM or CTX. There was only a 1.3-fold increase in tumor growth delay with UPHS and CDDP compared with CDDP alone. Carbogen breathing for 6 hours following drug administration had no significant effect on the tumor growth delay produced by CDDP. The combination of UPHS and carbogen breathing was a more effective addition to treatment with CDDP and resulted in a 1.9-fold increase in tumor growth delay from 7.4 to 14.1 days.

The addition of UPHS to treatment with BCNU increased the tumor growth delay produced by BCNU by 1.5-fold. Although carbogen breathing for 6 hours post drug administration increased the tumor growth delay produced by BCNU to a small degree, a much larger enhancement in tumor growth delay was observed with UPHS and carbogen breathing in combination with BCNU. The combination of UPHS/BCNU and carbogen resulted in a tumor growth delay of about 5.7 days, which was a 2.3-fold increase over the 2.5 days obtained with BCNU alone.

EXAMPLE II

Effects of UPHS on FSaII Fibrosarcoma Cell Toxicity and Bone Marrow Toxicity of PAM The procedures and materials of Example I were employed, except as noted. In this Example, tumors were allowed to grow to approximately 100 mm$^3$ in volume, which took about one week after tumor cell implantation. At this time, 0.3 ml of UPHS was injected via the tail vein. Immediately afterward, PAM was administered by intraperitoneal injection. The animals were then allowed to breath air or were placed in a circulating atmosphere of carbogen for 6 hours and then removed to air. The mice were sacrificed 24 hours after treatment to allow for full expression of drug cytotoxicity and repair of potentially lethal damage. The tumors were excised under sterile conditions and single cell suspensions were prepared for a colony forming assay. See Teicher, B. A. et al., "Approaches to Defining the Mechanism of Fluosol-DA 20%/Carbogen Enhancement of Melphalan Antitumor Activity", Cancer Res. 47:513–518 (1987); Teicher, B. A. et al., "Differential Enhancement of Melphalan Cytotoxicity in Tumor and Normal Tissue by Fluosol-DA and Oxygen Breathing", Int. J. Cancer 36:585–589 (1985); Teicher, B. A. et al., "Effects of Various Oxygenation Conditions on the Enhancement by Fluosol-DA of Melphalan Antitumor Activity", Cancer Res. 47:5036–5041 (1987); Teicher, B. A. and S. A. Holden, "A Survey of the Effect of Adding Fluosol-DA 20% / $O_2$ to Treatment with Various Chemotherapeutic Agents", Cancer Treat. Rep. 71:173–177 (1987), Teicher, B. A. et al., "Effect of Various Oxygenation Conditions and Fluosol-DA on Cancer Chemotherapeutic Agents", Biomat., Art. Cells and Art. Organs 16:533–546 (1988). One week later, the plates were stained with crystal violet and colonies of more than 50 cells were counted. The untreated tumor cell suspensions had a plating efficiency of 8–12%.

Bone marrow toxicity was determined as follows. Bone marrow was taken from the same animals used for the tumor excision assays and colony forming assays were carried out in the same manner. Colonies of at least 50 cells were scored on an acculite colony counter (Fisher, Springfield, N.J.). The results from three experiments, in which each group was measured in triplicate, were averaged.

Figure 1:
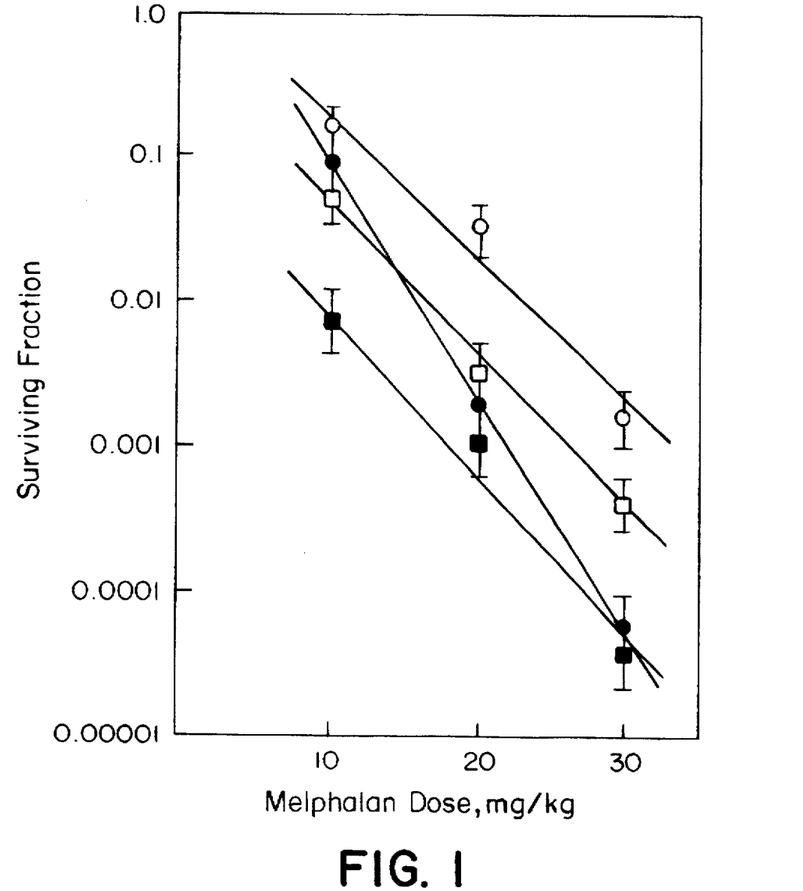
FIG. 1 is a plot of the surviving fraction of FSaIIC tumor cells and bone marrow granulocyte-macrophage colony forming units (CFU-GM) versus dose of Melphalan (PAM) administered to mice alone or with a single dose of ultrapurified polymerized bovine hemoglobin solution (UPHS) administered immediately prior to PAM injection.

The result for the tumor excision assays and bone marrow toxicity tests with PAM are plotted in FIG. 1 wherein the surviving fraction + SE of cells from the treated groups are compared to untreated controls.

PAM killed FSaIIC cells in a log-linear manner with increasing dose of PAM. With addition of UPHS to treatment with PAM at a dose of 10 mg/kg, there was about a 10-fold increase in tumor cell killing compared with PAM alone. At higher doses of PAM, the enhancement in tumor cell killing with the combination treatment disappeared indicating that whatever effect UPHS had to effect tumor cell killing could also be accomplished by increased dosage of the alkylating agent. In the bone marrow CFU-GM, the addition of UPHS to treatment with PAM produced a 3-fold increase in cell killing across the entire dosage range of PAM examined.

EXAMPLE III

Figure 2:
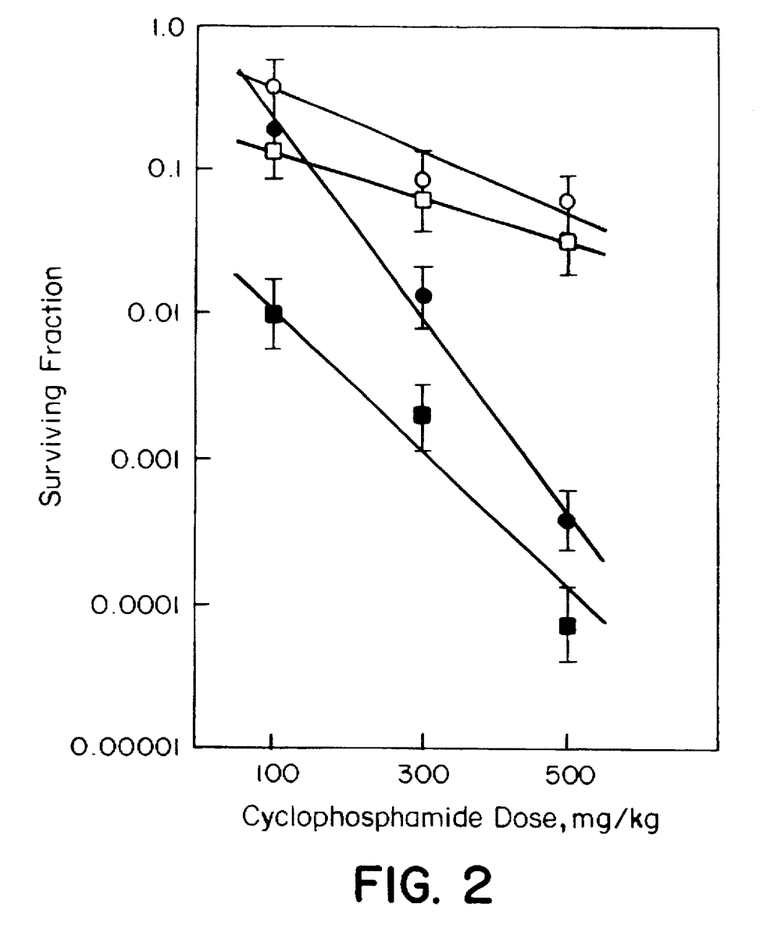
FIG. 2 is a plot of the surviving fraction of FSaIIC tumor cells and bone marrow CFU-GM versus dose of Cyclophosphamide (CTX) administered to mice alone or with a single dose of UPHS immediately prior to CTX injection.

Effects of UPHS on FSaII Fibrosarcoma Cell Toxicity and Bone Marrow Toxicity of CTX The procedures and materials of Example II were employed except that CTX was administered instead of PAM. The results are shown in FIG. 2.

CTX killed increasing numbers of FSaIIC cells with increasing doses of the drug. The addition of UPHS to treatment with a dose of 100 mg/kg of CTX resulted in about a 20-fold increase in the killing of FSaIIC cells. Although the differential between tumor cell kill by CTX alone and CTX plus UPHS decreased as the dose of CTX was increased, at the highest dose (500 mg/kg) of CTX examined, there was about 9-fold greater kill of FSaIIC tumor cells with the combined treatment. The addition of the UPHS to treatment with CTX resulted in a 2–3-fold increase in the toxicity of the drug to bone marrow CFU/gm.

EXAMPLE IV

Intracranial and Subcutaneous 9L Gliosarcoma

The 9L gliosarcoma has been widely used as a model for brain tumors. Barker. M. et al.. "Development of an Animal Brain Tumor Model and Its Response to Therapy with 1.3-Bis(2-chloroethyl)-1-nitrosourea", *Cancer Res.* 33:976–986 (1973) and Levin, V. A. et al., "Effectiveness of the Nitrosourea as a Function of Lipid Solubility for the Chemotherapy of Experimental Rat Brain Tumors", *Cancer Chemother. Rep.* 58:787–792 (1974). Furthermore, the 9L gliosarcoma growing subcutaneously in the hind leg of the Fisher 344 rat contains major areas of severe (<5 mmHg) hypoxia making up about 49% of the tumor.

The 9L gliosarcoma (9L) cells were obtained as a gift of 9L/SF gliosarcoma cells from Dr. Dennis Dean, University of California, San Francisco. These cells were maintained in culture in A-MEM (Grand Island Biological Co., Grand Island, N.Y.) and supplemented with 10% fetal bovine serum (Sterile Systems, Inc., Logan, Utah) and with antibiotics. The 9L cells ($4 \times 10^4$) in 10 µL of media without serum were implanted intracranially in male Fischer 344 rats (Taconic Farms, Germantown, N.Y.) weighing 200–250 gm on day 0. Each rat was anesthetized with sodium pentobarbital. A midline scalp incision was made and a hole was bored through the skull with 23 gauge needle at a point 2 mm lateral to the midline. The cell suspension was injected into the right frontal lobe at a depth of 3 mm from the dural surface. The needle was removed and the hole filled with dental cement. The scalp was sealed with a surgical clip. Two days later 9L cells ($2 \times 10^6$) were implanted subcutaneously into the flank of each animal. When the tumors were approximately 100 mm³ in volume, 7 days after tumor cell implantation, 8 ml/kg of UPHS was injected via the tail vein. After injecting the UPHS, administration of chemotherapeutic agents was initiated. CDDP therapy consisted of a single 8 mg/kg CDDP dose administered by intraperitoneal injection on day 7. BCNU therapy consisted of three 15 mg/kg BCNU doses administered by intraperitoneal injection days 7, 9 and 11. CTX and ifosfamide (IFOS) therapy consisted of three 100 mg/kg CTX or IFOS doses administered by intraperitoneal injection on days 7, 9 and 11. For the BCNU, CTX and IFOS therapies, UPHS was intravenously administered prior to each chemotherapeutic agent injection on days 7, 9 and 11. The IFOS was purchased from the Dana-Farber Cancer Institute. Survival of animals was monitored daily. Animals that were moribund or unable to reach food or water were killed by $CO^2$ inhalation.

The progress of each subcutaneous tumor was measured 3 times/week until it reached a volume of 500 mm³. Tumor growth delay was calculated as the number of days for each individual tumor to reach 500 mm³ compared with untreated controls. Each treatment group had 4 animals and the experiment was repeated twice. Days of tumor growth delay are the mean ± SE for the treatment group compared with the control.

The increases in life span for rats with intracranial 9L tumors are presented below in Table II.

TABLE II

Life Span Increase

| Treatment Group | Survival Days | % Increased from Control |
|---|---|---|
| Control Group | 26 ± 2.2 | 0% |
| UPHS | 27.8 | 7% |
| BCNU | 31.6 | 22% |
| BCNU/UPHS | 35.9 | 38% |
| CTX | 31.3 | 20% |
| CTX/UPHS | 37.2 | 43% |
| CDDP | 33.6 | 29% |
| CDDP/UPHS | 38.0 | 46% |
| IFOS | 30.9 | 19% |
| IFOS | 35.9 | 38% |

The effect of the treatments on the growth of the intracranial tumor was determined by the increase in life span of treated groups compared with the untreated controls. A percentage increase in life span of 25% or more is therapeutically significant. Although BCNU, CTX or IFOS alone improved the survival of the animals, the increase in life span did not reach significance. CDDP treatment alone resulted in a significant increase in life span. However with administration of UPHS prior to the BCNU, CTX, CDDP or IFOS therapy, substantially larger increases in life span of 38%, 43%, 46% and 38%, respectively, were achieved.

The subcutaneous 9L tumor growth was also evaluated. The results of the subcutaneous 9L tumor growth delay experiments are presented below in Table III.

TABLE III

Subcutaneous 9L Tumor Growth Delay

| Treatment Group | Mean Days |
|---|---|
| Control Group* | — |
| UPHS | 1.5 ± 0.4 |
| BCNU | 5.8 ± 0.5 |
| BCNU/UPHS | 7.8 ± 0.6 |
| CTX | 9.1 ± 0.7 |
| CTX/UPHS | 14.0 ± 0.9 |
| CDDP | 9.4 ± 0.8 |
| CDDP/UPHS | 10.1 ± 0.8 |
| IFOS | 10.4 ± 0.9 |
| IFOS/UPHS | 14.3 ± 1.0 |

* - Mean days for the control group to reach 500 mm³ were 19.5 ± 0.5 days.

Administration of UPHS alone did not significantly alter growth of the subcutaneous tumors. Administration of UPHS prior to treatment with BCNU resulted in a 1.3-fold increase in tumor growth delay compared to treatment with BCNU along. Similarly, administration of UPHS solution prior to each injection of CTX resulted in a 1.5-fold increase in tumor growth delay compared to treatment with CTX alone. There was no substantial effect on the tumor growth delay produced by a single dose of CDDP by administration of UPHS prior to the drug. Like CTX, the tumor growth delay resulting from treatment with IFOS was increased 1.4-fold by prior administration of UPHS.

The chemotherapeutic agents examined in this study were all relatively small molecules which should not be subject to blood brain barrier exclusion on the basis of molecular weight or charge. Two of the drugs CTX and IFOS, are pro-drugs which undergo metabolism in the liver to form short-lived active alkylating species. It is interesting that CTX and IFOS which were very effective treatments for subcutaneously growing 9L tumors were the least effective treatments for intracranial 9L tumors. BCNU was least effective against subcutaneously growing 9L tumors but moderately effective against the intracranial 9L tumors. CDDP which was the most stable and aqueously soluble drug studied was very effective against both subcutaneous and intracranial 9L tumors.

The addition of UPHS to treatment with the antitumor alkylating agents improved the overall therapeutic outcome of treatment of the intracranial tumors to a greater degree than it did treatment of the subcutaneous tumors. One possible reason for this differential effect may be that the intracranial tumors are much smaller (by necessity) than the subcutaneous tumors at the time of treatment. Another possible reason for a greater improvement in the intracranial tumors by the combined treatment may be that the brain (and perhaps the brain tumor) is more highly vascularized that the subcutaneous tumor.

The greatest increases in therapeutic response upon addition of UPHS to treatment with the antitumor alkylating agents were seen with CTX and IFOS as evidenced by both increase in tumor growth delay and increase in life span. Both BCNU and CDDP treatments were improved to a greater degree, as determined by increase in life span, against the intracranial tumor than against the subcutaneous tumor.

EXAMPLE V

Lewis Lung Carcinoma

The Lewis lung tumor was carried in male C57BL mice (Taconic Laboratories, Germantown, N.Y.). For the experiments, $2 \times 10^6$ tumor cells prepared from a brei of several stock tumors were implanted subcutaneously into the legs of male mice aged 8–10 weeks. by day 4 after tumor cell implantation, Lewis lung tumors began neovascularization. Animals bearing Lewis lung tumors were treated daily with i.p. Mino (10 mg/kg), Diflun (15 mg/kg) or Sulin (15 mg/kg) on days 4–18 following tumor implantation. When the tumors had reached a volume of approximately 100 mm³ in volume (day 7 after tumor cell implantation), cytotoxic therapy was initiated.

Therapy consisted of treatment with an antitumor alkylating agent, an antitumor antimetabolite, a non-steroidal anti-inflammatory drug (NSAID) and/or UPHS. CDDP and PAM therapy consisted of a single 10 mg/kg CDDP or PAM dose administered by intraperitoneal injection on day 7. CTX therapy consisted of three successive 150 mg/kg CTX doses administered by interperitoneal injections on days 7, 9 and 11. BCNU therapy consisted of three successive 15 mg/Kg BCNU doses administered by interperitoneal injections on days 7, 9 and 11. Therapy with the antimetabolite 5-fluorouracil (5-FU) consisted of 4 successive 40 mg/kg 5-FU doses administered by interperitoneal injections daily on days 7 to 11. The 5-FU was purchased from Sigma Chemical Co., St. Louis, Mo. Fourteen doses of 10 mg/kg of NSAID were administered daily by interperitoneal injections on days 4 to 18. UPHS was injected into the tail vein in 8 ml/kg doses daily on days 7–11.

The progress of each tumor was measured thrice weekly until it had reached a volume of 500 mm³. Tumor growth delay was calculated as the number of days required for each treated tumor to reach a volume of 500 mm³ as compared with untreated control tumors. Each treatment group comprised six animals and the experiment was repeated three times.

On the twentieth day after the subcutaneous tumor implantation, the delay in Lewis Lung Carcinoma tumor growth was evaluated. The results are presented in Table IV. Tumor growth delay data is presented as the mean value calculated for the treatment group as compared with the control group.

Neither the UPHS nor the NSAIDS, without a cytotoxic agent, had any significant effect on the subcutaneous growth of Lewis lung carcinoma. The tumor growth delay produced by CTX treatment was substantially longer than that resulting from CDDP, PAM, BCNU or 5-FU. However, the growth delay effects from treatment with CTX or PAM were substantially increased, more than two-fold, by the addition of UPHS to the treatment. CDDP, BCNU and 5-FU treatment was also enhanced, to a lesser degree, by the addition of UPHS to treatment.

Addition of NSAIDs to the cytotoxic agents, delayed tumor growth in an amount slightly less than that produced by the addition of UPHS to the cytotoxic agents, with sulin providing the best NSAID results. Furthermore, the combination of cytotoxic agents, NSAIDs and UPHS typically yielded the best results for most combinations with the growth delay for each cytotoxic agent generally doubled.

TABLE IV

Lewis Lung Carcinoma Growth Delay

| Treatment Group | WITHOUT UPHS | | WITH UPHS | |
|---|---|---|---|---|
| | Mean Days | Lung Metastases (% Large) | Mean Days | Lung Metastases (% Large) |
| Control | — | 20 (62) | 0.6 ± 0.3 | 18 (72) |
| Mino | 0.8 ± 0.3 | 20 (50) | 1.0 ± 0.4 | 20 (65) |
| Diflun | 0.3 ± 0.2 | 20 (51) | 0.9 ± 0.3 | 20 (55) |
| Sulin | 1.2 ± 0.4 | 19 (55) | 0.5 ± 0.3 | 21 (57) |
| CDDP | 4.5 ± 0.3 | 13 (58) | 5.7 ± 0.4 | 13 (40) |
| CDPP/Mino | 5.0 ± 0.3 | 11 (48) | 7.3 ± 0.8 | 16 (44) |
| CDDP/Diflun | 5.8 ± 0.5 | 15 (37) | 7.7 ± 0.9 | 16 (38) |
| CDDP/Sulin | 5.9 ± 0.5 | 13.5 (44) | 8.9 ± 1.0 | 13 (38) |
| CTX | 21.5 ± 1.7 | 12 (40) | 43.1 ± 2.9 | 8 (40) |
| CTX/Mino | 38.2 ± 2.9 | 6 (33) | 44.9 ± 3.2 | 3 (60) |
| CTX/Diflun | 31.5 ± 2.8 | 8 (38) | 38.4 ± 2.9 | 7 (50) |
| CTX/Sulin | 35.1 ± 2.6 | 10 (30) | 39.6 ± 2.8 | 5 (40) |
| PAM | 2.7 ± 0.3 | 13 (48) | 6.8 ± 0.4 | 10 (50) |
| PAM/Mino | 4.8 ± 0.4 | 11 (50) | 12.8 ± 0.9 | 9.5 (31) |
| PAM/Diflun | 5.0 ± 0.3 | 14 (40) | 9.4 ± 0.8 | 8 (50) |
| PAM/Sulin | 7.2 ± 0.4 | 12 (48) | 12.9 ± 0.9 | 9 (39) |
| BCNU | 3.6 ± 0.4 | 15.5 (53) | 5.3 ± 0.5 | 9 (61) |
| BCNU/Mino | 5.2 ± 0.6 | 15 (38) | 7.1 ± 0.6 | 8.5 (41) |
| BCNU/Diflun | 4.7 ± 0.5 | 12 (50) | 9.3 ± 0.8 | 8 (38) |
| BCNU/Sulin | 7.0 ± 0.6 | 12 (30) | 11.6 ± 0.9 | 7 (39) |
| 5-FU | 5.4 ± 0.4 | 21 (52) | 6.3 ± 0.5 | 15 (40) |
| 5-FU/Mino | 7.6 ± 0.6 | 18 (30) | 10.7 ± 0.8 | 11 (43) |
| 5-FU/Diflun | 6.5 ± 0.5 | 16.5 (44) | 11.6 ± 0.9 | 9.5 (53) |
| 5-FU/Sulin | 7.2 ± 0.6 | 15 (36) | 13.2 ± 1.1 | 9 (39) |

EXAMPLE VI

Effects of UPHS on Subcutaneous 9L Gliosarcoma Oxygenation

The procedures and materials of Example IV were employed, except as noted. In this Example, tumor $pO_2$ measurements were made under four conditions: 1) normal air breathing, 2) carbogen (95% $O_2$/5% $CO_2$) breathing, 3) 10 minutes post intravenous hemoglobin solution (8 ml/kg) administration with normal air breathing and 4) 15 minutes post the initiation of carbogen breathing after intravenous hemoglobin solution administration. Data collection through three tumor diameters accrued about 50 $pO_2$ measurements and took about 10 minutes. The $pO^2$ microelectrode was recalibrated in aqueous solutions saturated with air and 100% nitrogen after each data collection, therefore the $pO_2$ microelectrode was recalibrated 4 times during the course of the experiment. Recalibration requires about 15 minutes.

Therefore, the duration required for tumor $pO_2$ measurements under the four conditions tested was about one hour and 40 minutes.

Tissue oxygen measurements were made using a $pO_2$-Histograph (Eppendorf, Inc., Hamburg, Germany). The polarographic needle microelectrode was calibrated in aqueous solutions saturated with air and 100% nitrogen. The electrode was used for tumor measurements if there was less than 1% variation in current measurements upon repetition of the calibration cycle. For tumor measurements, the rat was anesthetized by an interperitoneal injection of Ketaset (35 mg/kg) and xylazine (25 mg/kg) prepared in phosphate-buffered 0.9% saline. The animal was placed on a heating pad and covered with a blanket to maintain body temperature. Core temperature was measured with a rectal thermometer. The tumor site was shaved and tumor diameters measured with calipers. A small patch of skin about 4 cm from tumor was shaved and an incision was made allowing the reference electrode (Ag/AgCl-ECG) to be inserted subcutaneously and secured. The tumor was exposed by removing about 1 $cm^2$ of skin over the site. The tumor capsis was then perforated with a 20 gauge needle. The $pO_2$ microelectrode was positioned in the perforation.

The $pO_2$ microelectrode under computer control was placed 1 mm into the tissue and then retracted 0.3 mm. Probe current was then measured and after 1.4 seconds the probe moved forward again. The total length of the measurement path was determined by the size of the tumor. After the probe reached the end of its measurement path it automatically retracted. The probe was then repositioned in the same perforation at a different angle and stepwise measurements were again initiated. Three diameters were measured in each tumor for a total of 40–60.

The results of the oxygenation measurements are presented in Table V, below.

TABLE V

Subcutaneous 9L Gliosarcoma Oxygenation

| Measurement Condition | % of readings <5 mmHg | 10th percentile | $pO_2$, mmHg Median | 90th percentile |
|---|---|---|---|---|
| W/out UPHS: | | | | |
| Air | 49 | 0.0 | 6.5 | 28 |
| Carbogen | 41 | 0.0 | 25 | 116 |
| With UPHS: | | | | |
| Air | 24 | 2.7 | 18 | 21 |
| Carbogen | 0 | 14.5 | 55 | 152 |

Oxygen tensions of less than 5 mmHg are considered severely hypoxic and probably represent regions of therapeutic resistance. Oxygen tensions in normally oxygenated tissues range from about 15–30 mmHg. Under normal air breathing conditions nearly half of the 9L tumor is severely hypoxic. Under carbogen breathing conditions the severely hypoxic regions were reduced to about 40% of the tumor while the median $pO_2$ increased about 4-fold to 25 mmHg. Administration of UPHS (8 ml/kg) markedly altered the oxygen profile of the tumors. With air breathing after administration of UPHS the percentage of severe hypoxia in the tumors was reduced to 24% and the median $pO_2$ reached 18 mm/Hg. The addition of carbogen breathing to administration of UPHS markedly increased the oxygenation of the tumor such that severe hypoxia was eliminated and oxygenation through 90% of the tumor was normal or greater than normal.

EXAMPLE VII

Comparison Between Effects of UPHS and a Perfluorocarbon Emulsion Employed in Combination with PAM The procedures and materials of Example I were employed except that Fluosol-DA was substituted for UPHS. Fluosol-DA was obtained from Alpha Therapeutics Corporation and is an emulsion consisting of 25% (w/v) of the following perfluorocarbons: 7 parts perfluorodecalin, 3 parts per perfluorotripropyliamine; Pluronic F-68 (2.7%, w/v); yolk phospholipids (0.4% w/v) as emulsifiers; and glycerol (0.8%, w/v) as a cryoprotective agent. The annex solution (electrolyte/bicarbonate solution) furnished the preparation with physiological osmolarity. The half-life of Fluosol-DA in vivo is about 12 hours.

The specific procedures employing Fluosol-DA have been described previously. See Teicher, B. A. et al., "Approaches to Defining the Mechanism of Fluosol-DA 20% -/Carbogen Enhancement of Melphalan Antitumor Activity", Cancer Res. 47:513–518 (1987); Teicher, B. A. et al., "Differential Enhancement of Melphalan Cytotoxicity in Tumor and Normal t+ Tissue by Fluosol-DA and Oxygen Breathing", Int. J. Cancer 36:585–589 (1985); and Teicher, B. A. et al., "Effects of Various Oxygenation Conditions on the Enhancement by Fluosol-DA of Melphalan Antitumor Activity", Cancer Res. 47:5036–5041 (1987).

When PAM (10 mg/kg) was administered to animals bearing the FSaIIC fibrosarcoma in combination with Fluosol-DA and air breathing a tumor growth delay of about 6.5 days was observed. If carbogen breathing for 1 hour post drug administration was added to therapy with Fluosol-DA and PAM a tumor growth delay of about 9.5 days resulted. Extending the carbogen breathing period to 6 hours did not alter the tumor growth delay produced by the PA< and Fluosol-DA combination (Teicher, B. A. et al., "Effect of Various Oxygenation Conditions and Fluosol-DA on Cancer Chemotherapeutic Agents", Biomat., Art. Cells and Art. Organs 16:533–546 (1988)), however, preparation of the PAM in the Fluosol-DA as a vehicle resulted in a much enhanced tumor growth delay of about 29.5 days with carbogen breathing. The addition of UPHS to treatment with PAM was not quite as effective as combining PAM with Fluosol-DA and carbogen breathing resulting in a tumor growth delay of about 6.9 days. The combination of UPHS and carbogen breathing with PAM was more effective than the combination of Fluosol-DA and carbogen breathing with PAM producing a tumor growth delay of about 11.1 days compared with about 9.5 days.

Six hours of carbogen breathing are necessary to obtain a significant enhancement in the growth delay of the FSaIIC fibrosarcoma produced by CTX. Teicher, B. A. et al., "The Effect of Fluosol-DA and Oxygenation Status on the Activity of Cyclophosphamide In Vivo" Cancer Chemother. Pharmacol. 21:286–291 (1988). In the case of this drug the growth delay of the FSaIIC tumor with the treatment combination of CTX (150 mg/kg) with Fluosol-DA and carbogen breathing for 6 hours was about 12 days compared with about 3.6 days with CTX alone. The 12 days of tumor growth delay obtained with this perfluorochemical emulsion/carbogen modulation of CTX was greater than the 7.4 days of tumor growth delay obtained with UPHS and air breathing with CTX but not as large as the 16.5 days of tumor growth delay obtained with the UPHS and carbogen breathing modulation of CTX.

EXAMPLE VIII

Increased Efficacy of Cytotoxic Therapy With Administration of Antiangiogenic Agents The current study was undertaken to examine the effect of TNP-470 and minocycline on oxygen delivery and response of subcutaneously implanted rat 9L gliosarcoma to cytotoxic therapy in the presence or absence of hemoglobin preparation.

Two of the major difficulties in the therapy of malignant brain tumors are the regional and clonal heterogeneity of human brain tumors within individual patients and the problem of the blood-brain barrier. The heterogeneity of brain tumors is responsible, at least in part, for the development of resistance to chemotherapeutic agents. Intrinsic variation in chemosensitivity has been demonstrated for human glioma cells, and low-dose nitrosourea therapy has been shown to rapidly result in resistant cell subpopulations. Tumor masses are also very heterogeneous in oxygenation and contain regions of hypoxia. Rampling, et al. reported the oxygen characteristics in the tumors of 20 patients with malignant brain tumors during open brain surgery performed under standard anesthetic conditions using the Eppendorf $pO_2$ polarographic oxygen microelectrode. Rampling, R. et al., *Int. J. Radiat. Oncol. Biol. Phys.*, 29:427–431 (1994). Sixteen of twenty tumors had hypoxic fractions, determined as percent of $pO_2$ values $\leq 2.5$ mmHg, of 20% or more (20%–69%). Twelve of twenty tumors had median $pO_2$'s of 5 mmHg or less (0.1–5.0). Hypoxia may be a significant factor in the short durations of response (<6 months) to radiation therapy and chemotherapy seen in brain tumor patients. Preclinical studies both in vitro and in vivo have established that hypoxia protects cells from the cytotoxic actions of radiation and many chemotherapeutic agents and thereby may be a significant factor in therapeutic resistance.

Potentiation of the efficacy of cytotoxic anticancer therapies by administration of antiangiogenic agents has been demonstrated in several in vivo experimental systems. Among the most promising of the antiangiogenic agents is TNP-470, a synthetic analog of the fungal antibiotic fumagillin. TNP-470 is a potent inhibitor of endothelial cell migration, endothelial cell proliferation and capillary tube formation. TNP-470 also inhibits angiogenesis as demonstrated in the chick embryo chorioallantoic membrane assay, the rabbit and the rodent cornea. TNP-470 has been shown to inhibit the growth of certain primary and metastatic murine tumors, as well as human tumor xenografts. The combination of TNP-470 and minocycline along with cytotoxic anticancer therapies formed particularly effective treatments for the Lewis lung carcinoma. Minocycline is a tetracycline and a matrix metallproteinase inhibitor, specifically a collagenase inhibitor which has demonstrated antiangiogenic activity. The characteristics of minocycline as a modulator of cytotoxic therapies in Lewis lung carcinoma have been described. Treatment of animals bearing the Lewis lung carcinoma with TNP-470/minocycline also resulted in increased oxygenation of the tumors.

It is not likely that increased delivery of oxygen from the vasculature will fully oxygenate most tumors. It has been well-established that the nitromidazole radiosensitizing agents, such as etanidazole, can act as selective cytotoxic drugs for hypoxic cells. In addition, these compounds, which are said to mimic the effect of oxygen in cells, have been shown to enhance the cytotoxicity of several antitumor alkylating agents including melphalan, cyclophosphamide, BCNU and 1-(2-chloroethyl)-3-cyclohexyl-1-nitrosourea in vitro and in vivo. This phenomenon has been termed chemosensitization.

Materials and Methods

Drugs. TNP-470, formerly called AGM-1470, was a gift from Takeda Chemical Industries, Ltd. (Osaka, Japan). Etanidazole was obtained as a gift from the Developmental Therapeutics Program of the National Cancer Institute (Bethesda, Md.). Minocycline and adriamycin (datnorubicin were purchased from SIGMA Chemical Co., Inc. (St. Louis, Mo.). Carmustine (BCNU) was purchased from the Dana-Farber Cancer Institute Pharmacy.

The hemoglobin solution (Biopure Corp., Boston, Mass.) is a polymerized form of a highly purified bovine hemoglobin solution that contains 13±2 gm/dl bovine hemoglobin. P50 measurements of the hemoglobin solution under conditions designed for testing human hemoglobin gave values of 34–37 mmHg. The hemoglobin component has a molecular mass range from 64 kDa (w/v) to 500 kDa (w/v). The hemoglobin solution also contains sodium (150 mM), chloride (110 mM) and potassium (4.0 mM) in a buffer solution (pH 7.6–7.9). The circulating half-life of the preparation is about 2 days.

Carbogen is 95% Oxygen and 5% Carbon Dioxide

Tumor. 9L/SF gliosarcoma cells were obtained as a gift from Dr. Dennis Deen (University of California, San Francisco, Calif.). 9L cells were maintained in culture in α-MEM (Grand Island Biological Co., Grand Island, N.Y.) supplemented with 10% fetal bovine serum (Sterile Systems, Inc., Logan, Utah) and antibiotics. For experiments, 9L cells ($2\times10^6$) were implanted subcutaneously into the hind-leg of female Fischer 344 rats. Teicher, B. A. et al., *Intl. J. Rad. Oncol. Biol. Phys.*, 15:1187–1192 (1988); Teicher, B. A. et al., *Cancer Chemother. Pharmacol.*, 33:57–62 (1993) and references cited therein.

Oxygen Measurements. Tissue oxygen measurements were made using a $pO_2$-Histograph (Eppendorf, Inc., Hamburg, Germany). The polarographic needle microelectrode was calibrated in aqueous solutions saturated with air or 100% nitrogen. The electrode was used for tumor measurements if there was less than 1% variation in current measurements upon repetition of the calibration cycle. For tumor $pO^2$ measurements, the rat was anesthetized by an i.p. injection of Ketaset (35 mg/kg) and rylazine (25 mlg/kg) prepared in phosphate-buffered 0.9% saline. The animal was placed on a heating pad and covered with a blanket to maintain body temperature. Core temperature was measured with a rectal thermometer. The tumor site was shaved and tumor diameters measured with calipers. A small patch of skin about 4 cm from tumor was shaved and an incision was made allowing the reference electrode (Ag/AgCl-ECG) to be inserted subcutaneously and secured. The tumor was exposed by removing about 1 $cm^2$ of skin over the site. The tumor capsis was performed with a 20-gauge needle. The $pO_2$ microelectrode was positioned in the perforation.

The $pO_2$ microelectrode under computer control was placed 1 mm into the tissue and then retracted 0.3 mm. Probe current was then measured and after 1.4 seconds, the probe moved forward again. The total length of the measurement path was determined by the size of the tumor. After the probe reached the end of its measurement path, it automatically retracted. The probe was then repositioned in the same perforation at a different angle and stepwise measurements again initiated. Three diameters were measured in each tumor for a total of 50–60 measurements.

Tumor $pO_2$ measurements were made under four conditions in animals pretreated with minocycline (10 mg/kg) i/p. daily for 5 days, TNP-470 (30 mg/kg) s.c. alternate days for 5 days, the combination of TNP-470 and minocycline or a single dose i.p. of BCNU (30 mg/kg) or adriamycin (5 mg/kg) 24 hrs. prior to the oxygen measurements or 24 hrs. after the final fraction of a radiation regimen consisting of 3 G ray daily for 5 days: 1) normal air breathing, 2) carbogen (95% $O_2/CO_2$ breathing, 3) 10 minutes post intravenous hemoglobin solution (8 ml/kg) administration with normal air breathing, and 4) 15 minutes post the initiation of carbogen breathing after intravenous hemoglobin solution administration. Data collection through three tumor diameters accrued about 50 $pO_2$ measurements and took about 10 minutes. The $pO_2$ microelectrode was recalibrated in aqueous solutions saturated with air and 100% nitrogen after each data collection; therefore, the $pO_2$ microelectrode was recalibrated 4 times during the course of the experiment. Recalibration requires about 15 minutes. Therefore, the duration required for tumor $pO_2$ measurements under the four conditions tested was about one hour and 40 minutes.

Tumor Growth Delay. Treatment was initiated when the subcutaneous tumors reached 100 $mm^3$ in volume. The anticancer drugs were administered i.p. BCNU (15 mg/kg) days, 7, 9 and 11 and adriamycin (1.75 mg/kg) daily days 7–11. Minocycline (10 mg/kg) was administered i.p. daily on days 4–18. TNP-470 (25 mg/kg) was administered s.c. alternate days for days 4–18. Fractionated radiation (5×3 Gray) was delivered daily on days 7–11 locally to the tumor-bearing hind-limb using a Gamma Cell 40 (Atomic Energy of Canada Ltd; dose rate 1 Gray/ruin). The hemoglobin solution (8 ml/kg) was administered i.v. prior to each fraction of radiation and prior to each dose of chemotherapy. Carbogen breathing was maintained for 1 hr. prior to and during radiation therapy delivery and for 6 hrs. after administration of chemotherapy in those groups receiving the hemoglobin solution. Etanidazole (1 g/kg) was administered i.p. alternate days on days 7, 9 and 11.

The progress of each subcutaneous tumor was measured 3 times/week until it reached a volume of 500 $mm^3$. Tumor growth delay was calculated as the number of days for each individual tumor to reach 500 $mm^3$ compared with the untreated controls. Each treatment group had 4 animals and the experiment was repeated twice. Days of tumor growth delay are the mean ± SE for the treatment group compared with the control.

Results

Tissue oxygen tensions were measured in the rat 9L gliosarcoma under normal air and carbogen breathing conditions prior to and after intravenous administration of the hemoglobin solution (8 ml/kg). As the effective oxygen delivery increased from air breathing to hemoglobin solution/air breathing and then to hemoglobin solution/ carbogen breathing, the median $pO_2$ in the tumor increased from 1.4 mmHg to 2.2 mmHg and then to 3 mmHg and the hypoxic fraction (% $pO_2$ readings<5 mmHg) decreased from 71% to 62% and then to 58%, respectively. While treatment of the tumor-breathing animals with minocycline (10 mg/kg) did not alter the oxygenation of the tumors, administration of TNP-470 (30 mg/kg) to the animals on alternate days for three injections resulted in a decrease in hypoxic fraction and increase in median $pO_2$ in the tumors under each of the four conditions tested but especially under the conditions of effective oxygen delivery. Administration of the combination of TNP-470/minocycline was most effective, resulting in median $pO_2$'s of 2.3 mmHg, 7 mmHg and 21.1 mmHg and hypoxic fractions of 64%, 46% and 30% as the oxygen delivery conditions were altered from air breathing to hemoglobin solution/air breathing and then to hemoglobin solution/carbogen, respectively.

It has been observed in other tumor systems that treatment with cytotoxic therapies results in increased tumor hypoxia. However, when rats bearing the 9L gliosarcoma growing subcutaneously in the hind-leg were treated with a single i.p. dose of BCNU (30 mg/kg) and tumor oxygenation measurements conducted 24 hrs. later, the tumors were slightly less hypoxic. Similarly, 24 hrs. after a single i.p. dose of adriamycin (5 mg/kg) the 9L tumors were less hypoxic under each of the four oxygenation conditions tested. Maximal tumor oxygenation post-administration of adriamycin was achieved with the hemoglobin solution/carbogen breathing with a median $pO_2$ of 15.6 mmHg and hypoxic fraction of 36%. On the other hand, 24 hrs. after the fifth fraction of a daily fractionated radiation therapy regime, the tumors were markedly more hypoxic with a median $pO_2$ of 0.0 mmHg and hypoxic fraction of 85%. Administration of the hemoglobin solution increased the median $pO_2$ to 3.8 and decreased the hypoxic fraction to 52%, the addition of carbogen breathing to administration of the hemoglobin solution resulted in a median $pO_2$ of 12.8 mmHg and a hypoxic fraction of 39%.

To assess the response of the tumor to these treatment combinations, the 9L gliosarcoma was implanted subcutaneously in the hind-leg in female Fischer 344 rats (Table VI). Treatment of the tumor-bearing animals with TNP-470 and minocycline alone or in combination for 2 weeks (days 4–18 post tumor implantation) resulted in modest tumor growth delay. BCNU (15 mg/kg×3) administered i.p. produced a tumor growth delay of 5.3 days that was increased to 9.9 days with the addition of TNP-470/minocycline to the regimen. Adriamycin (1.75 mg/kg×5) produced a tumor growth delay of 3.9 days that was increased to 10.6 days upon the addition of TNP-470/minocycline to the regimen. In those groups receiving the oxygen delivery agent, the hemoglobin solution (8 ml/kg) was administered along with each dose of the cytotoxic agent. Administration of the hemoglobin solution along with BCNU resulted in a tumor growth delay of 8.6 days that was increased to 9.1 days when carbogen breathing (6 hrs.) was maintained after drug injection. The tumor growth delay produced by the TNP-470/ minocycline/BCNU regimen increased to 10.4 days with administration of the hemoglobin solution and 16.4 days with the addition of carbogen breathing to that. Administration of the hemoglobin solution along with adriamycin resulted in a tumor growth delay of 5.6 days that was increased to 8 days with carbogen breathing (6 hrs.) after each drug injection. The tumor growth delay produced by the TNP-470/minocycline/adriamycin regimen was increased to 11.2 days by administration of the hemoglobin solution and to 17.0 days when carbogen breathing (6 hrs.) occurred after each adriamycin injection.

The 9L tumor is moderately responsive to radiation therapy. The fractionated radiation regimen (3 Gray daily for 5 days) resulted in a tumor growth delay of 4.8 days (Table I). Although administration of TNP-470/minocycline modestly increased the tumor growth delay produced by the radiation therapy, administration of the hemoglobin solution produced a 1.8-fold increase in tumor growth compared with radiation alone and the addition of carbogen for 1 hr. prior to and during radiation delivery produced 2.6-fold increase in tumor growth delay compared with radiation only. Etanidazole, which can act as an oxygen mimic and as a cytotoxic agent in hypoxic cells, administered 3 times over 5 days resulted in a 1.4-fold increase in the tumor growth delay produced by the radiation regimen. The regimen including TNP-470/minocyclinic along with etanidazole and fractionated radiation produced a 1.6-fold increase in tumor growth delay compared with radiation therapy alone. Finally, administering the hemoglobin solution along with the TNP-470/minocycline/etanidazole/etanidazole/ fractioned radiation regimen increased the tumor growth delay to 13.5 days, a 2.8-fold increase over the tumor growth delay obtained with radiation alone; and the addition of carbogen breathing for 1 hr. prior to and during the radiation delivery resulted in 20.5 days of tumor growth delay, a 4.3-fold increase in tumor growth delay compared with radiation therapy only.

A correlation between oxygenation and therapeutic response after treatment with radiation therapy and many chemotherapeutic agents has been recognized in preclinical solid tumor systems for some time. The 9L gliosarcoma has been widely used as a model for brain tumors. When grown subcutaneously in the hind limb of the Fischer 344 rat, the 9L tumor showed major areas of hypoxia. This tumor was responsive to administration of the hemoglobin solution/air breathing showing a 9% decrease in $pO_2$ readings $\leq 5$ mmHg and a further decrease in $pO_2$ readings $\leq 5$ mmHg of 13% when the animals were allowed to breath carbogen.

The ultrapurified polymerized bovine hemoglobin solution used in the current studies, when administered intravenously to C3H mice bearing the FSaIIC fibrosarcoma or to rats bearing the 13762 mammary carcinoma, has been shown to increase both the tumor growth delay and tumor cell killing by radiation therapy and by a variety of chemotherapeutic agents with little increase in the toxicity of these agents to the bone marrow. The intravenous administration of the hemoglobin solution decreased hypoxia in the rat 9L gliosarcoma carcinoma in untreated tumors and especially in chemotherapy and radiation therapy treated tumors. The tumor oxygenation data and the tumor growth delay data show a correlation between decreased hypoxia in the tumors and increased response to therapy.

TABLE VI

Growth delay of s.c. 9L gliossarcoma produced by antiangiogenic agents ± cytotoxic therapies with or without the hemoglobin solution.

| | Tumor growth delay, Days[a] | | |
|---|---|---|---|
| | | Hemoglobin solution (8 ml/kg)[b] | |
| Treatment Group | Air | Air | Carbogen[c] |
| TNP-470 (25 mg/kg × 6, sc) d 4–18[d] | 1.6 ± 0.3 | — | — |
| Minocycline (10 mg/kg × 14, ip) d 4–18 | 1.4 ± 0.3 | — | — |
| TNP-470/Minocycline | 2.0 ± 0.4 | 2.05 ± 0.4 | 3.7 ± 0.4 |
| BCNU(15 mg/kg × 3) d 7, 9, 11 | 5.3 ± 0.4 | 8.6 ± 0.7 | 9.1 ± 0.8 |
| TNP-470/BCNU | 7.0 ± 0.6 | — | — |
| Mino/BCNU | 5.8 ± 0.5 | — | — |
| TNP-470/Mino/BCNU | 9.9 ± 0.8 | 10.4 ± 0.9 | 16.4 ± 1.2 |
| Adriamycin (1.75 mg/kg × 5) d 7–11 | 3.9 ± 0.3 | 5.6 ± 0.6 | 8.0 ± 0.8 |
| TNP-470/Adria | 7.0 ± 0.5 | — | — |
| Mino/Adria | 6.7 ± 0.5 | — | — |
| TNP-470/Mino/Adria | 10.6 ± 0.8 | 14.2 ± 1.2 | 17.0 ± 1.4 |

TABLE VI-continued

Growth delay of s.c. 9L gliossarcoma produced by antiangiogenic agents ± cytotoxic therapies with or without the hemoglobin solution.

| | Tumor growth delay, Days[a] | | |
|---|---|---|---|
| | | Hemoglobin solution (8 ml/kg)[b] | |
| Treatment Group | Air | Air | Carbogen[c] |
| X-Rays (5 × 3 Gray)[e] | 4.8 ± 0.4 | 8.6 ± 0.8 | 12.3 ± 1.1 |
| TNP-470/X-Rays | 5.2 ± 0.5 | — | — |
| Mino/X-Rays | 4.9 ± 0.4 | — | — |
| TNP-470/Mino/X-Rays | 5.8 ± 0.5 | 10.8 ± 1.0 | 13.3 ± 1.4 |
| ETA (1 g/kg × 3)/ X-rays[f] | 6.6 ± 0.5 | 10.9 ± 1.1 | 14.6 ± 1.3 |
| TNP-470/Mino/ETA/ X-rays | 7.9 ± 0.8 | 13.5 ± 1.2 | 20.5 ± 1.7 |

[a]Mean days ± S.E.M. for treated tumors to reach 50 mm$^3$ compared with untreated controls. Control tumors reached 500 mm$^3$ in 19.9 ± 1.2 days.
[b]The hemoglobin solution is an ultrapurified bovine hemoglobin-based preparation (Hemopura, Biopure Corp.) containing 13 ± 1 gm/deciliter of bovine hemoglobin. P50 measurements of this preparation under conditions designed for testing human hemoglobin gave a value of 34 mmHg. The hemoglobin component has a molecular mass range from 64 kDa to 500 kDa. This material was administered via tail vein injection.
[c]The hemoglobin solution (8 ml/kg) was administered intravenously on days 7–11 in the treatment group receiving TNP-470/minocycline, on days 7, 9 and 11 just prior to BCNU in the groups receiving BCNU and on days 7–11 just prior to adriamycin or fractionated radiation therapy in the groups receiving adriamycin or radiation therapy. Carbogen breathing was maintained for 6 hrs. after each administration of the hemoglobin solution and chemotherapy. Carbogen breathing was maintained for 1 hour prior to and during radiation therapy delivery daily for 5 days.
[d]TNP-470 (25 mg/kg) was administered subcutaneously on alternate days, days 4–18. Minocycline (10 mg/kg) was administered intraperitoneally daily on days 4–18 post-tumor cell implantation.
[e]Radiation therapy was delivered locally to the tumor-bearing limb daily for 5 days in 3 Gray fractions using $^{137}Cs$ gamma rays (dose rate, 0.88 Gy/min). Animals were irradiated unanesthetized.
[f]Etanidazole (1 g/kg) was administered intraperitoneally on days 7, 9 and 11 prior to radiation delivery.

Equivalents

Those skilled in the art will recognize or be able to ascertain using no more than routine experimentation, many equivalents to the specific embodiments of the invention described herein. Such equivalents are intended to be covered by the following claims.

The invention claimed is:

1. A method for treating a tumor in a host with a chemotherapeutic agent which, when administered to said host, has an antitumor effect on said tumor, comprising:
   a) administering to said host a nonemulsified ultrapurified polymerized hemoglobin solution in an amount sufficient to significantly increase the antitumor effect of said agent; and
   b) administering to said host an effective amount of said chemotherapeutic agent.

2. A method of claim 1 wherein said tumor comprises a solid tumor.

3. A method of claim 1 wherein said tumor comprises leukemia.

4. A method of claim 1 wherein said chemotherapeutic agent comprises an antitumor alkylating agent.

5. A method of claim 1 wherein said chemotherapeutic agent comprises an antitumor antimetabolite.

6. A method of claim 1 wherein said hemoglobin comprises a hemoglobin which is dependent upon chloride ion concentration for oxygen transport.

7. A method of claim 6 wherein said host is a mammal.

8. A method of claim 7 wherein said mammalian host in human being.

9. A method of claim 1 wherein said hemoglobin is bovine hemoglobin.

10. A method of claim 1 wherein said chemotherapeutic agent comprises an antitumor alkylating agent.

11. A method of claim 1 wherein said host is a mammal.

12. A method of claim 11 wherein the host is breathing air.

13. In a method of treating a tumor in a mammalian host with an antitumor alkylating agent: the improvement being administering to said mammalian host, prior to treatment with said antitumor alkylating agent, an ultrapurified bovine hemoglobin solution in an amount sufficient to significantly increase the antitumor effect of said alkylating agent.

14. The improvement of claim 13 wherein said mammalian host is a human being.

* * * * *